United States Patent [19]

Shono et al.

[11] Patent Number: 4,523,994

[45] Date of Patent: Jun. 18, 1985

[54] BIS-CROWN-ETHER DERIVATIVES AND THEIR USE

[75] Inventors: Toshiyuki Shono, Suita; Keiichi Kimura, Osaka; Takumi Maeda, Nishinomiya, all of Japan

[73] Assignee: Shimadzu Corporation, Kyoto, Japan

[21] Appl. No.: 508,578

[22] Filed: Jun. 28, 1983

[30] Foreign Application Priority Data

Jun. 30, 1982 [JP] Japan ................... 57-114934

[51] Int. Cl.$^3$ ............... C08J 5/22; C08K 5/15
[52] U.S. Cl. ................... 210/500.2; 210/511; 210/643; 252/60; 521/88; 524/108; 549/352
[58] Field of Search ............ 524/108, 753, 754; 549/352; 252/60; 210/500.2, 511, 643; 521/88

[56] References Cited

U.S. PATENT DOCUMENTS

| | | | |
|---|---|---|---|
| 3,954,742 | 5/1976 | Snapp | 524/108 |
| 3,956,136 | 5/1976 | Frost | 210/500.2 |
| 3,987,061 | 10/1976 | Pedersen | 556/446 |
| 4,070,512 | 1/1978 | Lochmann | 524/108 |
| 4,256,859 | 3/1981 | Woo | 525/333.3 |
| 4,271,425 | 6/1981 | Wong | 524/566 |
| 4,313,865 | 2/1982 | Teramoto | 524/754 |
| 4,361,473 | 11/1982 | Young | 204/195 M |

FOREIGN PATENT DOCUMENTS

| | | |
|---|---|---|
| 122376 | 9/1981 | Japan . |
| 141312 | 11/1981 | Japan . |
| 57377 | 4/1983 | Japan . |

*Primary Examiner*—C. Warren Ivy
*Attorney, Agent, or Firm*—Hubbell, Cohen, Stiefel & Gross

[57] ABSTRACT

Bis-crown-ether derivatives having such configuration that the two crown rings may easily overlap spatially, holding a potassium or the like ion between them, and ion-selective membranes used for said bis-crown-ether derivatives as neutral carrier, which are useful as an ion sensor and are superior to the ion-selective membrane containing valinomycin.

15 Claims, 3 Drawing Figures

BIS-CROWN-ETHER DERIVATIVES AND THEIR USE

BACKGROUND OF THE INVENTION

1. Field of the Invention

The present invention relates to bis-crown-ether derivatives and their use, particularly the use for ion-selective membranes for potassium-selective electrodes or the like.

2. Description of the Prior Art

Generally speaking, ion-selective electrodes are those electrodes which indicate concentration or activity of a specific ion in a solution by membrane potential of membrane electrodes, as represented by glass electrodes for the measurement of pH.

Now, the potassium-ionic concentration in a living body has a close relation with metabolic reactions in the living body, and so the measurement of this ionic concentration is frequently utilized for the diagnosis of various diseases such as hypertensive diseases, renal diseases, nerval disturbances and the like, as well as the dialysis of blood. The measurement has hitherto been effected mainly by the use of the spectrum method such as flame analysis.

However, such spectrum method required not only a large-size instrument but also a significant amount of time for the measurement and accordingly was not suited for being carried out in the actual place of diagnosis. Thus there has been a continuing need for the development of a simple method for the quick measurement of potassium ion and a small-size instrument. Although a method utilizing a liquid membrane comprising an antibiotic valinomycin as neutral carrier dissolved in an aromatic organic solvent has been but to practical use for this purpose, valinomycin is still a very expensive compound. Further, for the preparation of practical, useful potassium-selective electrodes, a high ionic selectivity for potassium ion not disturbed by sodium ion or ammonium ion which in many cases co-exists with the potassium ion is required.

The inventors of the present invention have already published on the ion-selective membranes for potassium-selective electrodes using, as neutral carrier, bis(15-crown-5) compounds containing benzene rings ie benzo-crown rings (J. Electroanal. Chem., 95 (1979), 91–101). However, improvement in durability and response time of these electrodes has been required, though their high selectivity for potassium ion has been recognized.

The present invention has been made to solve these problems and the main purpose thereof resides in providing ion-selective membranes for potassium-selective electrodes, which use bis(15-crown-5) compounds containing benzo-crown rings as neutral carrier and enable one to perform measurement of potassium ion simply and quickly for a long duration of time with high selectivity and accuracy.

SUMMARY OF THE INVENTION

According to the present invention, there are provided bis-crown-ether derivatives of the general formula (I):

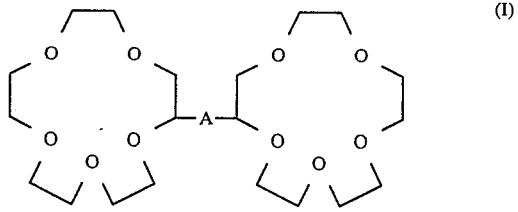

(in which A represents a divalent organic group which may take such configuration that the two crown rings may easily overlap spatially, holding a monovalent metal ion having ionic radius of 1.3–2.1 Å between them, like a sandwich), and ion-selective membranes containing as neutral carrier at least one of the compounds of the general formula (I). The monovalent metal ion as mentioned above includes potassium [ionic radius (coordinate valence): 1.52(6)], rubidium [1.63(6)], cesium [1.84(6)] and thallium [1.64(6)] [cf. R. D. Shannon, C. T. Prewitt, Acta Crystallogr., B25 925–946(1969)], among which potassium is preferable.

This bis(15-crown-5) derivatives in the present invention are per se novel compounds which have never been disclosed in prior art.

DESCRIPTION OF THE PREFERRED EMBODIMENTS

Figure 1:
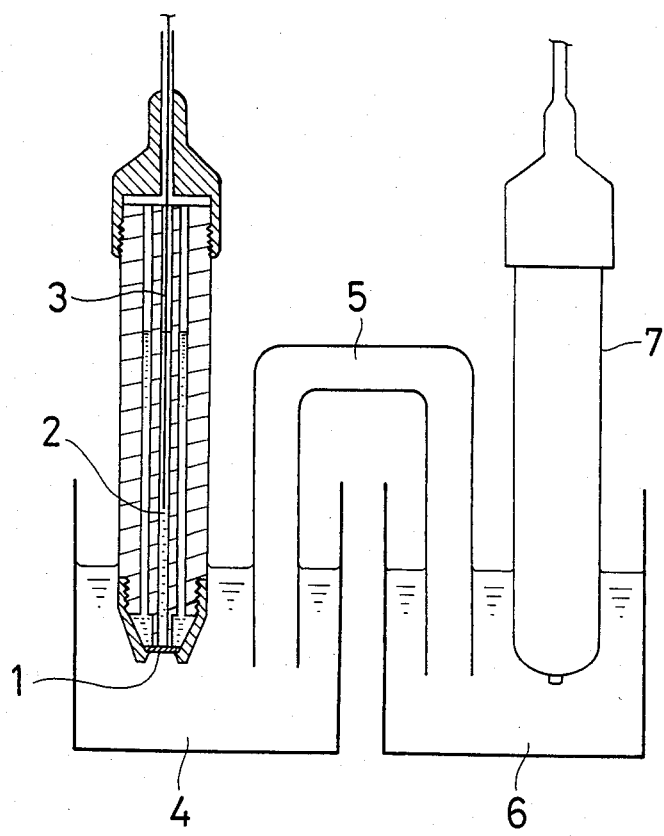
FIG. 1 is a schematic drawing which includes a section showing an example of the construction of electrodes using as neutral carrier bis-crown-ether derivatives of the present invention.

As "A" in the above general formula (I), groups represented by a sub-formula (II):

(in which Z represents a radical $-CH_2O-CO-$, $-CO-O-$, $-CH_2O-$ or $-CONH-$ and Y represents a divalent aliphatic group which may be substituted) are suitable. Further, as "Y" in the above sub-formula (II),

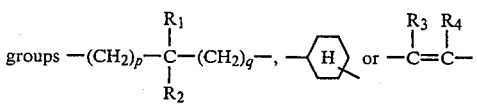

(in which $R_1$ and $R_2$ each represents a hydrogen atom or an alkyl group of $C_1-C_{20}$, p and q each represents 0 or an integer of 1, 2 or b 3, $R_3$ and $R_4$ take mutually cis-configuration and each represents a halogen atom, a lower alkyl group or an aryl group, and the two bonds of the cyclohexylene group are at cis-position) are preferred. As embodiments of preferable bis-crown-ether derivatives of the present invention, there can be mentioned those compounds which are represented by the following general formulae (III)–(VII):

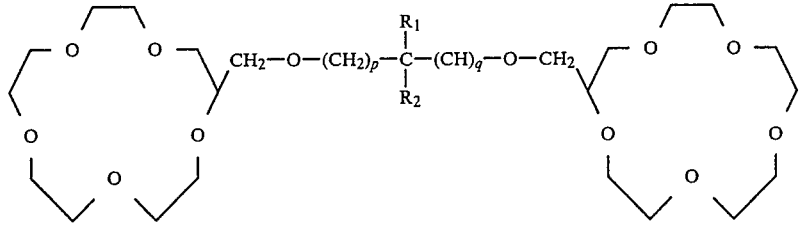 (III)

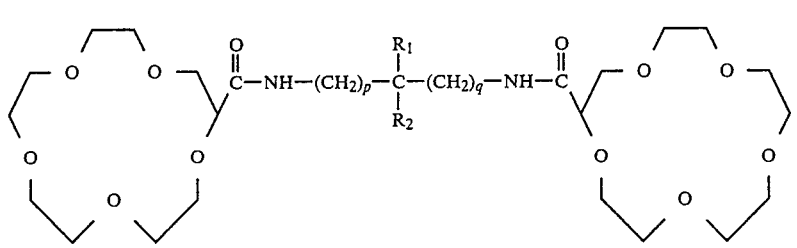 (IV)

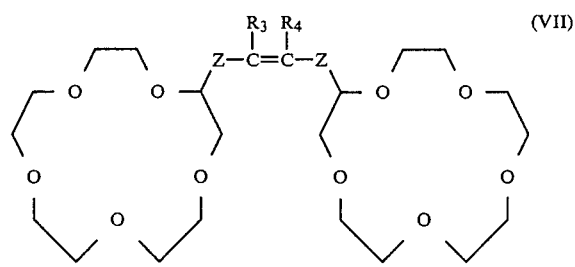 (V)

(in the formulae (III)–(V), $R_1$ and $R_2$ each represents a hydrogen atom or an alkyl group of $C_1$–$C_{20}$, and p and q each represents 0 or an integer of 1, 2 or 3)

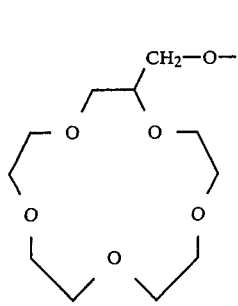 (VI)

(in which, Z represents a group —CH₂O—CO—, —CO—O—, —CH₂O— or —CONH—, and the two bonds of the cyclohexylene group are at cis-position)

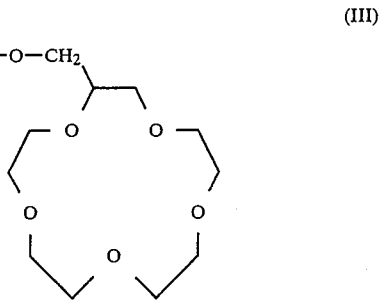 (VII)

(in which, Z represents a group —CH₂O—CO—, —CO—O—, —CH₂O— or —CONH—, and $R_3$ and $R_4$ take mutually cis-configuration and each represents a halogen atom, a lower alkyl group or an aryl group).

In addition, the alkyl group $R_1$ or $R_2$ in the above described formulae (III)–(V) may be a phenyl-substituted alkyl group of $C_1$–$C_{20}$, such as benzyl group of phenethyl group.

Such compounds represented by the general formula (I) are obtained by reacting a 15-crown-5 having a functional group such as halogenoalkyl group, aldehyde group, carboxyl group, alkoxyl group, etc. with a diol, dicarboxylic acid or diamine which may be substituted, under the conventional conditions for the condensation or substitution. More specifically, they are obtained for example by reacting well known hydroxymethyl-15-crown-5, crown-carboxylic acid, crown-aldehyde or the like with a dicarboxylic acid such as malonic acid, adipic acid, etc. or a diol, which may be substituted.

The compounds of the present invention as mentioned above are characterized in that the two crown ring units are in such configuration as to preferentially form a sandwich-like construction by holding potassium or the like ion between them.

The ion-selective membranes of the present invention may be used in the form of solid membrane or liquid membrane. The solid membrane may be formed by dispersing the above-mentioned bis-crown compound homogeneously in a water-insoluble solid organic polymer as carrier. The polymer is desired to have a property of forming a matrix for supporting the bis-crown compound, a neutral carrier, in the form of a membrane and preventing elution of the neutral carrier into an aqueous solution to be measured or the like. At the same time, the polymer is desired to have a property of enabling proper dispersion of potassium or the like ion contained in the aqueous solution to be measured into the matrix. As such polymer are used polyvinyl chloride, silicone rubber, polymethyl methacrylate and the like, usually.

Ion-selective membranes comprising polyvinyl chloride as carrier are usually formed by dissolving polyvinyl chloride, plasticizers and the bis-crown compounds in a suitable organic solvent having a lower boiling point such as tetrahydrofuran and evaporating the solvent gradually, for example, in a Petri dish. The plasticizers are used for the purpose of giving a suitable flexibility to the membranes obtained. For instance, dioctyl phthalate, o-nitrophenyl octyl ether and the like are used.

Ion-selective membranes can be prepared also, as in the case of those comprising silicone rubber as carrier, by dissolving the bis-crown compounds, silicone rubber and silane compounds for cross linking the rubber in a suitable organic solvent, polymerizing and molding into the form of membrane, and removing the solvent from the molding.

The bis-crown compounds are contained in the solid membrane in an amount of 0.5–20% by weight, preferably 1–15% by weight. If the content of the bis-crown compounds were too low, the response would be inferior. If it were too high, homogeneous dispersion into the polymer would be difficult, to say nothing of the increased expense. In the case that plasticizers are used together, as the case of using polyvinyl chloride as carrier, they are used preferably in an amount of 50–70% by weight.

The liquid membrane may be formed by dissolving the bis-crown compound in an water-insoluble polar organic solvent, and higher aliphatic alcohols, aromatic hydrocarbons having nitro-group or halogen as substituent, aliphatic hydrocarbons having nitro-group or halogen as substituent, aromatic ethers and the like are used as said polar organic solvent. As preferred embodiments, there can be mentioned 1-decanol, nitrobenzene, chlorobenzene, diphenyl ether, 1,2-dichloroethane, etc. The content of the bis-crown compounds in the liquid membrane is 0.5–20% by weight, preferably 1–10% by weight, for the same reason as mentioned above. The liquid membrane is usually used by holding it in a porous support made of ceramics or cellulosics. Porous film comprising fluorine-contained resin such as teflon is also one of the preferred supports.

The ion-selective membranes of the present invention use, as described above, the bis(15-crown-5) compounds having a linking portion of a prescribed chain length, as neutral carrier. Such bis-crown compounds form stable 2:1 sandwich complexes (the ratio of crown ring:ion is 2:1) specifically and selectively with potassium or the like ion, regardless of the presence of interfering ions such as sodium ion, ammonium ion or the like. Therefore, the ion-selective membranes of the present invention enable measuring potassium-ion concentration or activity with high selectivity, short response time and superior reproducibility. Thus, they are ion-selective membranes for potassium-selective electrodes of high practical value. Also, an ion-selective field effect transistor (IS-FET; cf. J. Appl. phys., 49, 58(1980), Matsuo et al) may be prepared by forming the ion-selective membrane of the invention on the gate insulator of FET.

In addition, the bis-15-crown-5 compounds represented by the general formula (I) of the present invention may be useful also as antibacterial agent.

Next, representative examples of the process of preparing bis-15-crown-5 compounds used in the present invention are shown.

PREPARATION EXAMPLE 1

Various bis-15-crown-5 compounds of the general formula (III) in which $R_1$ and $R_2$ each represents an alkyl group and $p=q=o$ have been prepared.

A solution of diethyl dialkylmalonate (5 m mol) in ethanol was added to a solution of hydroxymethyl-15-crown-5 (10.5 m mol) and metallic potassium (0.5 m mol) in ethanol, and the mixture was stirred at 80° C. for 24 hours. After completion of the reaction, the mixture was filtered and then the solvent was evaporated under reduced pressure. The residue obtained was dissolved in chloroform to give 5% solution, and the aimed product of the general formula (III) in which $R_1=R_2=$alkyl group and $p=q=o$ was isolated and purified by GPC. Some physical data of the products so obtained are shown in Table 1.

TABLE 1

(The case wherein $R_1=CH_3$, $R_2=C_{12}H_{25}$, $p=q=o$)
Mass (m/e)=751
$^1$HNMR (δ-ppm, CCl$_4$): 0.88(3H, t), 1.24(20H, m), 1.35(3H, s), 1.75(2H, m), 3.4–3.9(38H, m), 4.03(4H, d).
IR(cm$^{-1}$): 2920+2850(s), 1730(s), 1460(m), 1360(m), 1250(m), 1130+1100(s), 1080(sh), 920(m), 840(m), 730(m).

(The case wherein $R_1=C_2H_5$, $R_2=C_2H_5$, $p=q=o$)
Mass (m/e)=624
$^1$HNMR(δ-ppm, CDCl$_3$): 0.81(6H, t), 1.86(4H, q), 3.4–3.9(38H, m) 4.03(4H).
IR(cm$^{-1}$): 2910+2860(s), 1730(s), 1450(m), 1360(m), 1300(m), 1240(m), 1120+1100(s), 920(m), 850(m), 680(m).

(The case wherein

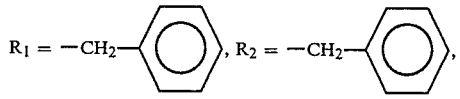

$p=q=o$)
Mass (m/e)=748
$^1$HNMR(δ-ppm, CDCl$_3$): 3.23(4H, s), 3.66(38H, m), 4.00(4H, m) 7.23(10H, s).
IR(cm$^{-1}$): 3030(w), 2920+2860(s), 1730(s) 1600(w), 1500(m), B 1450(m), 1360(m) 1280+1260(m), 1140+1100(s), 980(w), 920(w), 770(m), 740(m), 700(m).

PREPARATION EXAMPLE 2

A solution of a glycol (1.4 mmol) having a proper chain length and sodium hydride (2.8 mmol) in tetrahydrofuran was heated under reflux, and thereto was added dropwise a solution in tetrahydrofuran of bromomethyl-15-crown-5 (2.9 mmol). Refluxing was continued for 24 hours. After completion of the reaction, the reaction mixture was filtered and the solvent was evaporated under reduced pressue to give an oily residue. The residue was dissolved in chloroform to give 5% solution, and the desired product was isolated and purified by GPC to give a bis-15-crown-5 compound of the general formula (IV).

Various bis-crown-ether compounds of the general formulae (III)–(VII) obtained in the above Preparation Examples 1 and 2 and those obtained by the same processes as described in said Examples are shown in Table 2, together with their mass spectrum and the results of their elemental analysis.

In the column of elemental analysis values, calculated values are shown in the upper row and analytical values in the lower row.

TABLE 2

| Corresponding formula | Compound No. | Conditions | Molecular formula | Properties (Melting point °C.) | Mass spectrum Molecular ion m+ | Elemental analysis values | | C | H | N | O |
|---|---|---|---|---|---|---|---|---|---|---|---|
| general formula (III) | 1 | $R_1 = R_2 = H$<br>$p = q = 0$ | $C_{25}H_{44}O_{14}$ | Liquid | 568 | Calculated value | | 52.82 | 7.79 | — | 39.39 |
| | | | | | | Analytical value | | 52.71 | 8.01 | — | — |
| | 2 | $R_1 = R_2 = H$<br>$p = q = 1$ | $C_{27}H_{48}O_{14}$ | Liquid | 596 | Calculated value | | 54.35 | 8.11 | — | 37.54 |
| | | | | | | Analytical value | | 53.97 | 8.27 | — | — |
| | 3 | $R_1 = R_2 = C_2H_5$<br>$p = q = 0$ | $C_{29}H_{52}O_{14}$ | Liquid | 624 | Calculated value | | 55.75 | 8.38 | — | 35.85 |
| | | | | | | Analytical value | | 55.49 | 8.37 | — | — |
| | 4 | $R_1 = CH_3$,<br>$R_2 = C_{12}H_{25}$,<br>$p = q = 0$ | $C_{38}H_{70}O_{14}$ | Liquid | 751 | Calculated value | | 60.77 | 9.39 | — | 29.82 |
| | | | | | | Analytical value | | 60.88 | 9.21 | — | — |
| | 5 | $R_1 = CH_3$,<br>$R_2 = C_{14}H_{29}$,<br>$p = q = 0$ | $C_{40}H_{74}O_{14}$ | Liquid | 779 | Calculated value | | 61.67 | 9.57 | — | 28.75 |
| | | | | | | Analytical value | | 61.44 | 9.63 | — | — |
| | 6 | $R_1 = R_2 =$ 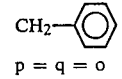<br>$p = q = 0$ | $C_{39}H_{56}O_{14}$ | Liquid | 748 | Calculated value | | 62.55 | 7.53 | — | 29.91 |
| | | | | | | Analytical value | | 62.19 | 7.61 | — | — |
| | 7 | $R_1 = R_2 =$ 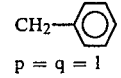<br>$p = q = 1$ | $C_{41}H_{60}O_{14}$ | Liquid | 777 | Calculated value | | 63.38 | 7.78 | — | 28.83 |
| | | | | | | Analytical value | | 63.01 | 7.81 | — | — |
| | 8 | $R_1 = CH_3$,<br>$R_2 = C_{18}H_{37}$,<br>$p = q = 0$ | $C_{44}H_{82}O_{14}$ | Liquid | 834 | Calculated value | | 63.30 | 9.83 | — | 26.85 |
| | | | | | | Analytical value | | 63.15 | 9.80 | — | — |
| general formula (IV) | 9 | $R_1 = R_2 = H$<br>$p = q = 0$ | $C_{23}H_{44}O_{12}$ | Liquid | 512 | Calculated value | | 53.89 | 8.65 | — | 37.45 |
| | | | | | | Analytical value | | 53.72 | 8.69 | — | — |
| | 10 | $R_1 = R_2 = H$<br>$p = q = 1$ | $C_{25}H_{48}O_{12}$ | Liquid | 540 | Calculated value | | 55.53 | 8.94 | — | 35.51 |
| | | | | | | Analytical value | | 55.23 | 9.11 | — | — |
| | 11 | $R_1 = R_2 =$<br>$C_2H_5$,<br>$p = q = 0$ | $C_{27}H_{52}O_{12}$ | Liquid | 568 | Calculated value | | 57.02 | 9.21 | — | 33.75 |
| | | | | | | Analytical value | | 56.87 | 9.11 | — | — |
| | 12 | $R_1 = CH_3$,<br>$R_2 = C_{15}H_{25}$,<br>$p = q = 0$ | $C_{36}H_{70}O_{12}$ | Liquid | 695 | Calculated value | | 62.22 | 10.15 | — | 27.62 |
| | | | | | | Analytical value | | 62.65 | 10.02 | — | — |
| | 13 | $R_1 = CH_3$,<br>$R_2 = C_{14}H_{29}$,<br>$p = q = 0$ | $C_{38}H_{74}O_{12}$ | Liquid | 723 | Calculated value | | 63.12 | 10.31 | — | 26.55 |
| | | | | | | Analytical value | | 63.07 | 10.29 | — | — |
| | 14 | $R_1 = R_2 =$ 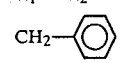<br>$p = q = 0$ | $C_{37}H_{56}O_{12}$ | Liquid | 692 | Calculated value | | 64.14 | 8.14 | — | 27.71 |
| | | | | | | Analytical value | | 63.99 | 7.98 | — | — |
| general formula (V) | 15 | $R_1 = CH_3$,<br>$R_1 = C_{12}H_{25}$<br>$p = q = 0$ | $C_{36}H_{68}N_2O_{12}$ | Liquid | 720 | Calculated value | | 60.00 | 9.44 | 3.88 | 26.66 |
| | | | | | | Analytical value | | 59.98 | 9.40 | 3.85 | — |
| | 16 | $R_1 = CH_3$,<br>$R_2 = C_{12}H_{25}$,<br>$p = q = 1$ | $C_{38}H_{72}N_2O_{12}$ | Liquid | 748 | Calculated value | | 60.96 | 9.62 | 3.74 | 25.66 |
| | | | | | | Analytical value | | 61.01 | 9.58 | 3.71 | — |

TABLE 2-continued

| Corresponding formula | Compound No. | Conditions | Molecular formula | Properties (Melting point °C.) | Mass spectrum Molecular ion m+ | Elemental analysis values | | C | H | N | O |
|---|---|---|---|---|---|---|---|---|---|---|---|
| general formula (VI) | 17 | Z = CH$_2$—O—C(=O)— (1,2-cis form) | C$_{30}$H$_{52}$O$_{14}$ | Liquid | 636 | Calculated value | | 56.59 | 8.23 | — | 35.17 |
| | | | | | | Analytical value | | 56.39 | 8.31 | — | — |
| | 18 | Z = —CO—O— (1,2-cis form) | C$_{28}$H$_{48}$O$_{14}$ | Liquid | 608 | Calculated value | | 55.25 | 7.94 | — | 36.79 |
| | | | | | | Analytical value | | 55.02 | 8.01 | — | — |
| | 19 | Z = —CONH— (1,2-cis form) | C$_{28}$H$_{50}$N$_2$O$_{12}$ | Solid m.p. (91–92° C.) | 580 | Calculated value | | 57.91 | 8.67 | 0.34 | 33.06 |
| | | | | | | Analytical value | | 57.61 | 8.59 | 0.37 | — |
| general formula (VII) | 20 | Z = —CH$_2$—O—C(=O)— R$_3$ = R$_4$ = Cl | C$_{26}$H$_{42}$O$_{14}$Cl$_2$ | Liquid | 580 | Calculated value | Cl | 53.78 | 7.29 | 0.34 | 38.57 |
| | | | | | | Analytical value | | 53.51 | 7.01 | 0.29 | — |
| | 21 | Z = —CH$_2$—O—C(=O)— R$_3$ = R$_4$ = C$_2$H$_5$ | C$_{30}$H$_{52}$O$_{14}$ | Liquid | 636 | Calculated value | | 56.59 | 8.23 | — | 35.17 |
| | | | | | | Analytical value | | 56.23 | 7.99 | — | — |
| | 22 | Z = —CH$_2$—O—C(=O) R$_3$ = R$_4$ = C$_6$H$_5$ | C$_{38}$H$_{52}$O$_{14}$ | Liquid | 732 | Calculated value | | 62.28 | 7.15 | — | 30.56 |
| | | | | | | Analytical value | | 69.88 | 7.21 | — | — |

In the following, the present invention is explained by giving Examples. The invention, however, shall not be limited thereto.

EXAMPLE 1

10 mg of a bis-crown-ether of the general formula (III) in which R$_1$=CH$_3$, R$_2$=C$_{12}$H$_{25}$ and p=q=o (Compound No. 4), 100 mg of o-nitrophenyl octyl ether and 40 mg of polyvinyl chloride were dissolved in 3 ml of tetrahydrofuran, and then tetrahydrofuran was spontaneously evaporated in a Petri dish at room temperature to prepare an ion-selective membrane comprising polyvinyl chloride as carrier. This membrane was cut into a round shape having a diameter of 3 mm and set to the lower part of Orion Model 92 electrode. Then, using a standard Calomel electrode as the external reference electrode and setting an cell formulation of Ag-.AgCl/0.001 MKCl/membrane/sample solution/0.1 MNH$_4$NO$_3$/KCl (saturated)/Hg$_2$Cl$_2$.Hg, as shown in FIG. 1, the activity of potassium-ion in the standard solution and the potential difference between electrodes were measured to prepare the calibration curve. All measurements including the above case were carried out at 25°±1° C., using a Corning pH meter, type 130.

In FIG. 1, (1) represents an ion-selective membrane of the present invention comprising polyvinyl chloride as carrier, (2) represents the inner solution, (3) represents the internal electrode comprising Ag—AgCl, (4) represents the solution to be measured, (5) represents the salt bridge, (6) represents the solution for liquid-junction and (7) represents Calomel electrode.

The calibration curve obtained was rectilinear in the pK range of 5–1 and indicated Nernst's response. There was no significant effect of pH in the pH range of 3–11.

Next, the selectivity coefficient $K_{KM}$ for interfering ion M$^+$ was pursued according to the mixed solution method. That is, while maintaining the activity of an interfering ion M$^+$ in the sample solution at a constant $a_M^+$ (100 m mol as ion concentration), the activity of potassium ion was varied and the potential difference between electrodes was measured in search of specific intercept activity of potassium ion $a_K^+$ (cf. "SELECTIVE ION SENSITIVE ELECTRODES" Chapter 2, Section 3, G. J. Moody, J. D. R. Thomas, Merrow Publishing Co., Ltd. England). The selectivity coefficient was obtained by dividing the $a_K^+$ by $a_M^+$. That is, $K_{KM}^+ = a_K^+/a_M^+$.

The selectivity coefficient values for various interfering cations of the above ion-selective membrane are shown in Table 4 with that of a comparative example.

TABLE 4

| | | Comparative Example | |
|---|---|---|---|
| Interfering cation | Membrane of Example 1 | Using valinomycin as neutral carrier | Using compound of the following formula (VIII) as neutral carrier |
| Li$^+$ | 1.0 × 10$^{-4}$ | 2.6 × 10$^{-4}$ | 3.3 × 10$^{-4}$ |
| Na$^+$ | 2.0 × 10$^{-4}$ | 3.7 × 10$^{-4}$ | 5.8 × 10$^{-4}$ |
| Rb$^+$ | 3.2 × 10$^{-2}$ | 3.6 | 8.2 × 10$^{-2}$ |
| Cs$^+$ | 1.8 × 10$^{-2}$ | 5.2 × 10$^{-1}$ | 4.1 × 10$^{-3}$ |
| NH$_4^+$ | 7.0 × 10$^{-3}$ | 1.8 × 10$^{-2}$ | 9.2 × 10$^{-3}$ |
| Mg$^{2+}$ | 1.6 × 10$^{-4}$ | 1.1 × 10$^{-4}$ | 1.6 × 10$^{-4}$ |
| Ca$^{2+}$ | 1.6 × 10$^{-4}$ | 1.4 × 10$^{-4}$ | 4.6 × 10$^{-4}$ |
| Sr$^{2+}$ | 2.8 × 10$^{-4}$ | 1.4 × 10$^{-4}$ | 1.2 × 10$^{-4}$ |
| Ba$^{2+}$ | 1.2 × 10$^{-4}$ | 1.4 × 10$^{-4}$ | 1.3 × 10$^{-4}$ |
| Ni$^{2+}$ | 1.6 × 10$^{-4}$ | 2.0 × 10$^{-4}$ | 2.3 × 10$^{-4}$ |
| Co$^{2+}$ | 1.8 × 10$^{-4}$ | 2.6 × 10$^{-4}$ | 2.3 × 10$^{-4}$ |
| Cu$^{2+}$ | 1.2 × 10$^{-4}$ | 3.6 × 10$^{-4}$ | 1.3 × 10$^{-4}$ |
| Fe$^{2+}$ | 1.6 × 10$^{-4}$ | 1.4 × 10$^{-4}$ | 1.3 × 10$^{-4}$ |

The selectivity coefficient for sodium ion, KKNa, was 2×10$^{-4}$ as the mean value obtained by two experiments. This indicates that the ion-selective membrane has a sensibility to potassium ion of $1/(2\times 10^{-4})$ times, i.e. 5000 times as high as that to sodium ion.

$KK_{NH_4}$ determined in the same way was $7\times 10^{-3}$. This shows a very high sensitivity for potassium ion. The response time and the durability are also excellent as shown in Table 3.

Although the conventionally used bis-crown-ethers containing benzene rings (such as the bis-crown-ether of the formula (VIII) shown below) were tested in the same way, their response time $t_{90}$ was 3–5 minutes.

Figure 2:
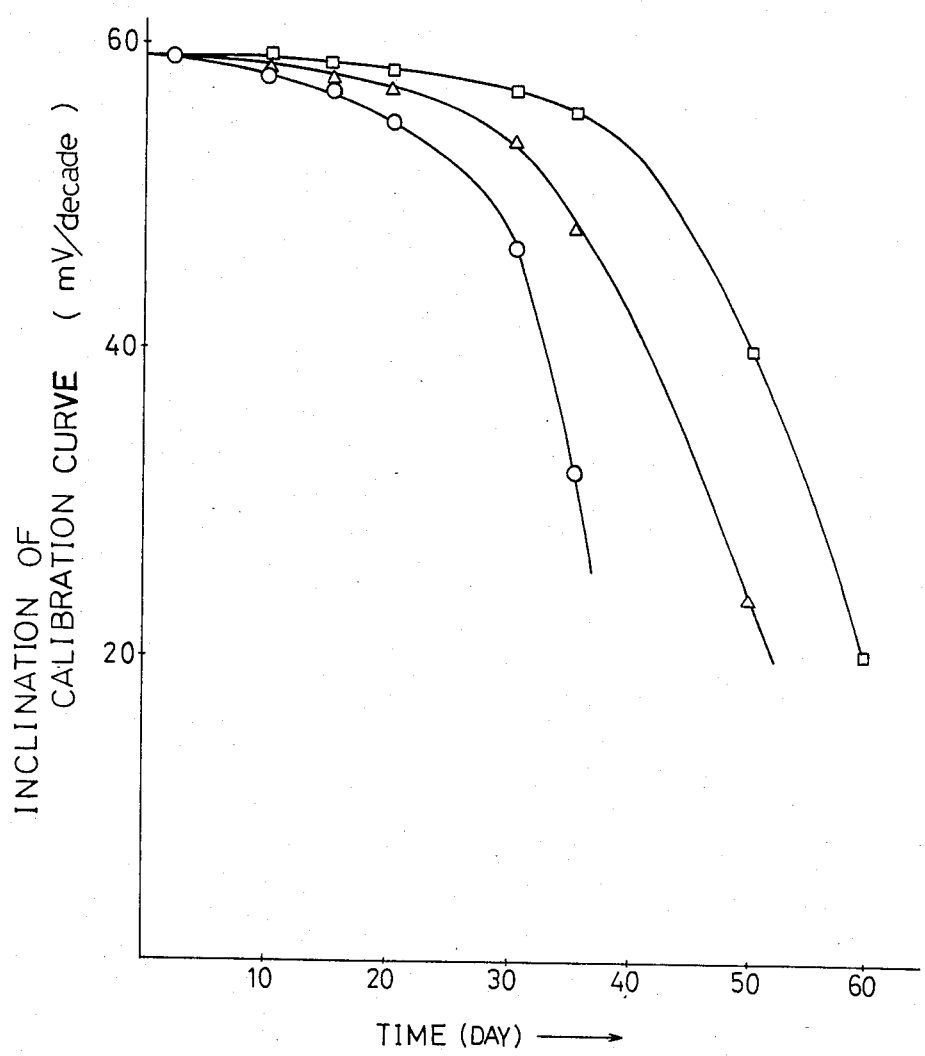
FIG. 2 is a graph showing the durability of a ion-selective membrane of the present invention along with that of comparative examples.

In FIG. 2 are shown the results of durability tests under the conditions accelerating deterioration of ion-selective membranes which were carried out using test samples (KCl $10^{-2}$ mol) containing surface activating agents such as Triton X. In this FIG. 2 □ represents the results obtained by using the compounds of the present invention as described above, Δ represents the results obtained by using the conventional valinomycin and O represents the results obtained by using the bis-crown-ether of the following formula (VIII) containing benzene rings:

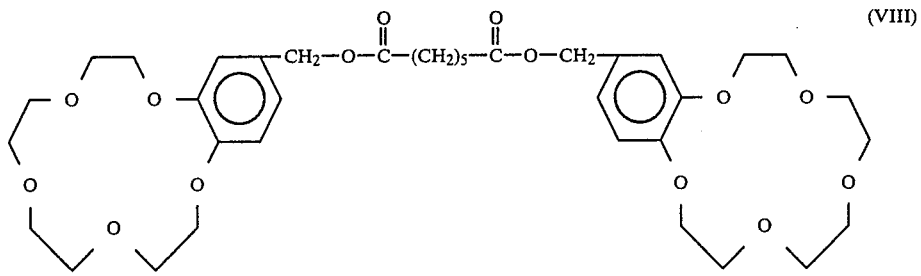

It is understood also from these results that the ion-selective membranes of the present invention have excellent durability as compared with conventional ones and can be used over a period of several months for the measurement of potassium-ionic concentration in actual objects such as urine, blood serum and the like.

TABLE 3

| Variation of potassium-ionic concentration | $t_{90}$ (minutes) | $E_{av}$ (mv) | $E_{dev}$ (mv) |
| --- | --- | --- | --- |
| $10^{-6} \to 10^{-4}$ (M) | <0.5 | −279 | <±1 |
| $10^{-4} \to 10^{-2}$ (M) | <1.0 | −174 | <±1 |
| $10^{-2} \to 10^{0}$ (M) | <1.0 | −73 | <±1 |

$t_{90}$:time required to reach 90% of the final indicator potential as measured for the aqueous solution having 100 times higher concentration, after the electric potential has been fixed for the aqueous solution having the lower potassium-ionic concentration.

$E_{av}$:mean value of the electric potentials indicated by the solution having higher concentration, as electric potentials were measured alternately for the two aqueous solutions having potassium-ionic concentrations mutually different by 100 times. $E_{dev}$:deviation from the above $E_{av}$ of the individual value obtained by measurement.

On the other hand, the membrane of valinomycin is not affected by organic substances in blood such as protein enzyme, sugar and the like. Similarly, no substantial effect by the organic substances in blood was observed on the ion-selective membrane in accordance with the invention.

EXAMPLE 2

Solid membranes were prepared in the same way as described in Example 1, using various bis-crown-ether compounds of the present invention shown in FIG. 2 as neutral carrier, and their KKNa values were measured.

The selectivity coefficient values are shown in Table 4.

TABLE 4

| Compound No. | KkNa | Compound No. | KkNa |
| --- | --- | --- | --- |
| 1 | $9 \times 10^{-3}$ | 12 | $5 \times 10^{-4}$ |
| 2 | $9 \times 10^{-3}$ | 13 | $6 \times 10^{-4}$ |
| 3 | $5 \times 10^{-4}$ | 14 | $9 \times 10^{-4}$ |
| 4 | $2 \times 10^{-4}$ | 15 | $2 \times 10^{-3}$ |
| 5 | $3 \times 10^{-4}$ | 16 | $8 \times 10^{-3}$ |
| 6 | $3 \times 10^{-4}$ | 17 | $8 \times 10^{-4}$ |
| 7 | $2 \times 10^{-3}$ | 18 | $7 \times 10^{-4}$ |
| 8 | $5 \times 10^{-4}$ | 19 | $3 \times 10^{-3}$ |
| 9 | $8 \times 10^{-3}$ | 20 | $4 \times 10^{-3}$ |
| 10 | $3 \times 10^{-3}$ | 21 | $3 \times 10^{-3}$ |
| 11 | $6 \times 10^{-4}$ | 22 | $5 \times 10^{-3}$ |

EXAMPLE 3

A solution containing 5% by weight of the same bis-crown-ether as used in Example 1 in nitrobenzene was prepared. Using this solution as liquid membrane, calibration curve and KKNa value were pursued with the same cell formulation as Example 1. The calibration curve indicated Nernst's response in the pK range of 5–1, and the KKNa value was $3\times 10^{-4}$.

EXAMPLE 4

The effect of flow rate of sample solution on potential response was measured by using a flow-through type potassium-selective electrode which comprises the ion-selective membrane of Example 1. An aqueous mixture of sodium chloride (140 mmol/l) and potassium chloride (4 mmol/l) was used as a sample solution. The result is shown in FIG. 3 with comparative example.

Figure 3:
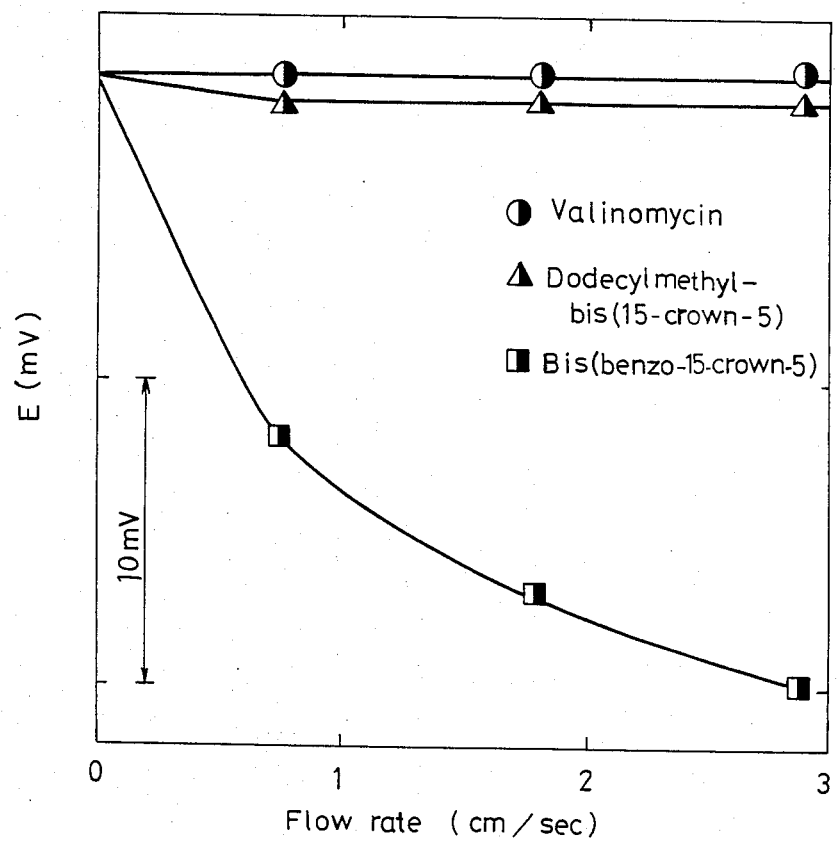
FIG. 3 is a graph showing the effect of flow rate on potential response of the $K^+$-selective electrode of the present invention, along with that of comparative examples.

As is clear from FIG. 3, the comparative potassium-selective electrode based on bis(benzo-15-crown-5) (VIII) showed a considerable variance upon flow rate of the solution, but the electrode based on dodecyl methyl bis(15-crown-5) of the invention showed stable potential, as found in the valinomycin electrode. Accordingly, the membrane of the invention is judged to possess high practical value.

What is claimed is:

1. An ion-selective membrane comprising at least one bis-crown-ether derivative of the general formual (I):

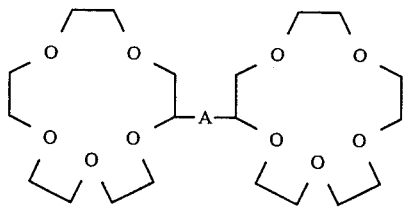
(I)

wherein A represents a divalent organic group which may take such a configuration that the two crown rings may easily overlap spatially, holding a monovalent metal ion having an ionic radius of 1.3–2.1 Å between them, like a sandwich.

2. An ion-selective membrane comprising a bis-crown-ether derivative as defined in claim 1 represented by the formula (III):

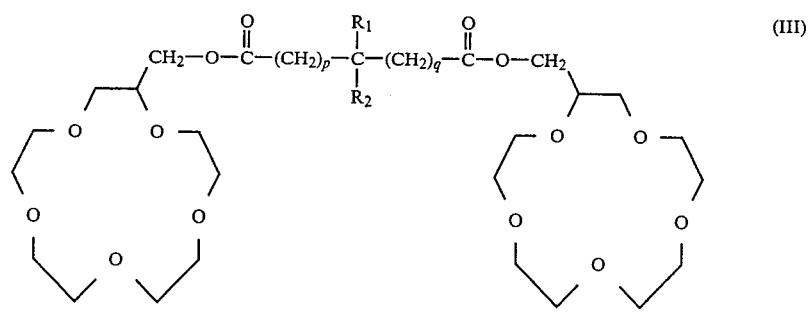
(III)

wherein $R_1$ and $R_2$ each represents a hydrogen atom or an alkyl group of $C_1$–$C_{20}$, and p and q each represents 0 or an integer of 1, 2 or 3.

3. An ion-selective membrane comprising a bis-crown-ether derivative as defined in claim 1 represented by the formula (IV):

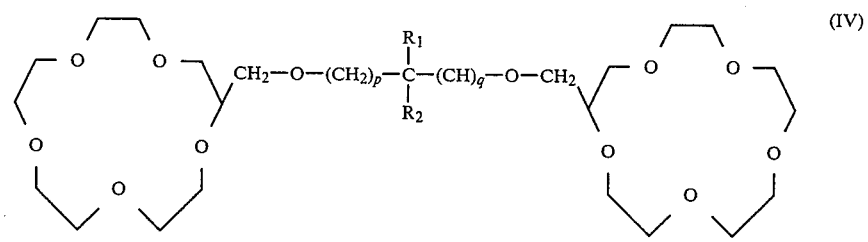
(IV)

wherein $R_1$ and $R_2$ each represents a hydrogen atom or an alkyl group of $C_1$–$C_{20}$, and p and q each represents 0 or an integer of 1, 2 or 3.

4. An ion-selective membrane comprising a bis-crown-ether derivative as defined in claim 1 represented by the formula (V):

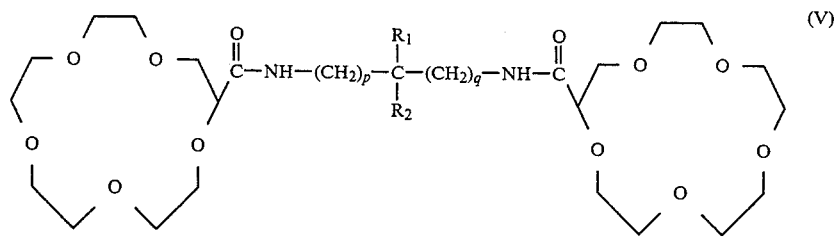
(V)

wherein $R_1$ and $R_2$ each represents a hydrogen atom or an alkyl group of $C_1$–$C_{20}$, and p and q each represents 0 or an integer of 1, 2 or 3.

5. An ion-selective membrane comprising a bis-crown-ether derivative as defined in claim 1 represented by the general formula (VI):

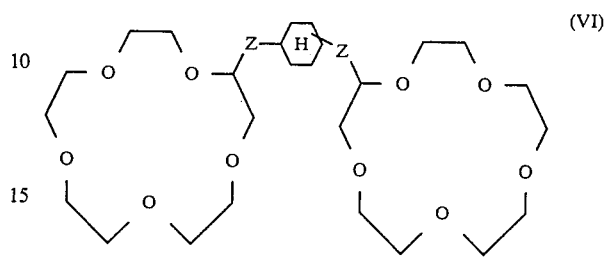
(VI)

wherein Z represents a group —CH₂O—CO—, —CO—O—, —CH₂O— or —CONH—, provided that the two bonds in the cyclohexylene group are at cis-positions.

6. An ion-selective membrane comprising a bis-crown-ether derivative as defined in claim 1 represented by the formula (VII):

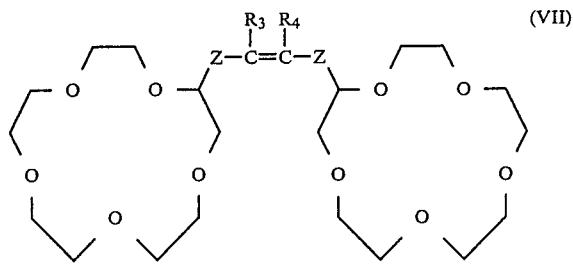

wherein the group A in the formula (I) is a group represented by the sub-formula (II):

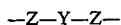

wherein Z represents a —CH₂O—CO—, —CO—O—, —CH₂O— or —CONH— group and Y is a group represented by the formula:

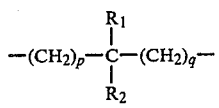

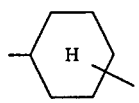

or

wherein R₁ and R₂ each represents a hydrogen atom or an alkyl group of C₁–C₂₀, p and q each represents 0 or an integer of 1, 2, or 3, R₃ and R₄ take a mutually cis-configuration and each represents a halogen atom, a lower alkyl group or an aryl group and the two bonds of the cyclohexylene group are at cis-position.

7. An ion-selective membrane comprising a bis-crown-ether derivative of the formula:

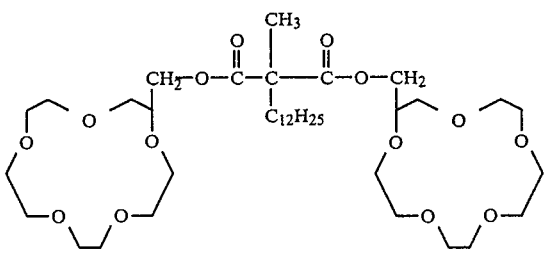

8. An ion-selective membrane of claim 1, wherein the bis-crown-ether derivative is dispersed in a water-insoluble organic polymer as the carrier and is made to form a solid membrane.

9. An ion-selective membrane of claim 8, wherein the water-insoluble organic polymer is polyvinylchloride, silicone rubber or polymethacrylate.

10. An ion-selective membrane of claim 1, wherein the bis-crown-ether derivative is dissolved in a water-insoluble polar organic solvent as the carrier and is made to form a liquid membrane.

11. An ion-selective membrane of claim 10, wherein the water-insoluble polar organic solvent is a higher aliphatic alcohol, an aromatic hydrocarbon substituted by nitro-group or halogen, an aliphatic hydrocarbon substituted by nitro-group or halogen, or an aromatic ether.

12. An ion-selective membrane of claim 1 which is a potassium ion selective membrane.

13. An ion sensor comprising the ion-selective membrane of claim 1.

14. An ion sensor according to claim 13, wherein the ion sensor is a potassium-selective electrode.

15. An ion-selective membrane comprising the bis-crown-ether derivative as defined in claim 1, wherein the group A in the formula (I) is a group represented by the sub-formula (II):

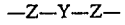   II wherein Z represents a —CH₂O—CO—, —CO—O—, —CONH— group and Y is a group represented by the formula:

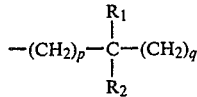

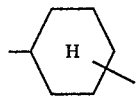

or

wherein R₁ and R₂ each represents a hydrogen atom or an alkyl group of C₁–C₂₀, p and q each represents 0 or an integer of 1, 2 or 3, R₃ and R₄ take a mutually cis-configuration and each represents a halogen atom, a lower alkyl group or an aryl group, and the two bonds of the cyclohexylene group are at cis-position.

* * * * *

UNITED STATES PATENT AND TRADEMARK OFFICE
CERTIFICATE OF CORRECTION

PATENT NO.  : 4,523,994
DATED       : June 18, 1985
INVENTOR(S) : TOSHIYUKI SHONO ET AL.

It is certified that error appears in the above—identified patent and that said Letters Patent is hereby corrected as shown below:

Column 2, line 26: insert --the-- after "in".

Column 4, line 35: change "of" (2nd occurr) to --or--.

Column 6, line 47: omit "B"; line 60, change "pressue" to --pressure--.

Column 13, lines 11-15, delete "wherein... sandwich." and substitute the following therefor:

--wherein the group A in the formula (I) is a group represented by the sub-formula (II):

-Z-Y-Z- wherein z represents a $-CH_2O-CO-$, $-CO-O-$, $-CH_2O-$ or $-CONH-$ group and Y is a group represented by the formula:

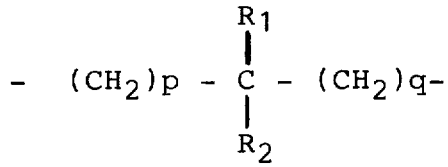

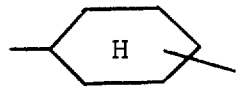

or

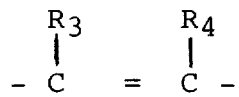

UNITED STATES PATENT AND TRADEMARK OFFICE
CERTIFICATE OF CORRECTION

PATENT NO. : 4,523,994
DATED : June 18, 1985
INVENTOR(S) : TOSHIYUKI SHONO ET AL.

It is certified that error appears in the above—identified patent and that said Letters Patent is hereby corrected as shown below:

wherein $R_1$ and $R_2$ each represents a hydrogen atom or an alkyl group of $C_1-C_{20}$, p and q each represents 0 or an integer of 1, 2 or 3, $R_3$ and $R_4$ take a mutually cis-configuration and each represents a halogen atom, a lower alkyl group or an aryl group and the two bonds of the cyclohexylene group are at cis-position Column 15, lines 13-42, delete "wherein... cis-position. and substitute the following therefor:

--wherein Z represents a group - $CH_2O-CO-$, $-CO-O-$, $-CH_2O-$ or $-CONH-$, and $R_3$ and $R_4$ take mutually cis-configuration and each represents a halogen atom, a lower alkyl group or an aryl group.--.

Signed and Sealed this

Nineteenth Day of November 1985

[SEAL]

Attest:

DONALD J. QUIGG

Attesting Officer

Commissioner of Patents and Trademarks